United States Patent
Ketelson et al.

(10) Patent No.: US 8,846,641 B2
(45) Date of Patent: *Sep. 30, 2014

(54) STABILIZED OPHTHALMIC GALACTOMANNAN FORMULATIONS

(71) Applicant: Alcon Research, Ltd., Fort Worth, TX (US)

(72) Inventors: Howard Allen Ketelson, Dallas, TX (US); James W. Davis, Suwanee, GA (US); David L. Meadows, Colleyville, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/892,429

(22) Filed: May 13, 2013

(65) Prior Publication Data

US 2013/0244971 A1 Sep. 19, 2013

Related U.S. Application Data

(63) Continuation of application No. 13/100,439, filed on May 4, 2011, now abandoned.

(60) Provisional application No. 61/331,511, filed on May 5, 2010.

(51) Int. Cl.
| | |
|---|---|
| *A61K 31/736* | (2006.01) |
| *A61K 9/00* | (2006.01) |
| *A61K 9/08* | (2006.01) |
| *A61K 45/06* | (2006.01) |

(52) U.S. Cl.
CPC ............ *A61K 31/736* (2013.01); *A61K 9/0048* (2013.01); *A61K 9/08* (2013.01); *A61K 45/06* (2013.01)
USPC .......................................................... 514/54

(58) Field of Classification Search
USPC .......................................................... 514/54
See application file for complete search history.

(56) References Cited

U.S. PATENT DOCUMENTS

| | | | | |
|---|---|---|---|---|
| 4,136,173 | A | | 1/1979 | Pramoda et al. |
| 5,456,745 | A | * | 10/1995 | Roreger et al. ............ 106/140.1 |
| 5,505,953 | A | * | 4/1996 | Chowhan ...................... 424/427 |
| 6,403,609 | B1 | * | 6/2002 | Asgharian ..................... 514/310 |
| 6,444,199 | B1 | * | 9/2002 | Renn ........................... 424/78.26 |
| 7,084,130 | B2 | * | 8/2006 | Shah et al. ...................... 514/54 |
| 2008/0138310 | A1 | | 6/2008 | Ketelson et al. | |
| 2010/0196415 | A1 | | 8/2010 | Davis et al. | |

FOREIGN PATENT DOCUMENTS

| | | |
|---|---|---|
| WO | 2004/112750 | 12/2004 |
| WO | 2008/036855 | 3/2008 |

OTHER PUBLICATIONS

Bradley et al., "Thermal Degradation of Guar Gum", Carbohydrate Polymers, vol. 10:205-214, 1989.
Cheng et al., "Characterization and Intermolecular Interactions of Hydroxypropyl Guar Solutions", Biomacromolecules, vol. 3(3):456-461, 2002.
Franz et al., "Chemical Stability of Some Model Polysaccharides", Macromolecular Symposia, vol. 120:169-181, 1997.
Gebert et al., "Purified Guar Galactomannan as an Improved Pharmaceutical Excipient", Pharmaceutical Development and Technology, vol. 3(3):315-323, 1998.
Gittings et al., "The Effect of Solvent and Ions on the Structure and Rheological Properties of Guar Solutions", Journal Physical Chemistry, vol. 105:9310-9313, 2001.
Khomutov et al., "Thermal Degradation of Polysaccharides", Russian Journal of Applied Chemistry, vol. 67(4)Part 2:574-577, 1994.
Kok et al., "Viscosity of Galactomannans During High Temperature Processing: Influence of Degradation and Solubilization", Food Hydrocolloids, vol. 13:535-542, 1999.
Rao et al., "Effect of Heat Treatment on the Flow Properties of Aqueous Guar Gum and Sodium Carboxymethylcellulose Solutions", Journal of Food Science, vol. 46:897-899, 1981.
Vega-Cantu et al., "Effect of Magnesium and Iron on the Hydration and Hydrolysis of Guar Gum", Biomacromolecules, vol. 7:441-445, 2006.
Whitcomb et al., "Rheology of Guar Solutions", Journal of Applied Polymer Science, vol. 25:2815-2827, 1980.

\* cited by examiner

*Primary Examiner* — Ganapathy Krishnan
(74) *Attorney, Agent, or Firm* — Mark F. Flanigan

(57) ABSTRACT

The present invention relates to viscosity stabilized ophthalmic formulations and ophthalmic formulations suitable for drug delivery. The formulations comprise galactomannans such as guar or hydroxypropyl guar and a borate source such as boric acid. The formulations further comprise a diol alcohol such as sorbitol and, optionally, a pharmaceutically acceptable divalent cation salt such as magnesium chloride.

15 Claims, No Drawings

STABILIZED OPHTHALMIC GALACTOMANNAN FORMULATIONS

CROSS-REFERENCE TO RELATED APPLICATION

This application is a Continuation (CON) of U.S. application Ser. No. 13/100,439, filed May 4, 2011, priority of which is claimed under 35 U.S.C. §120, the contents of which are incorporated herein by reference. This application also claims priority under 35 U.S.C. §119 to U.S. Provisional Patent Application No. 61/331,511, filed May 5, 2010, the entire contents of which are incorporated herein by reference.

TECHNICAL FIELD OF THE INVENTION

The present invention relates to ophthalmic formulations comprising galactomannans, and more specifically to formulations comprising galactomannan and a diol alcohol compound in a quantity sufficient to stabilize the viscosity of the formulation.

BACKGROUND OF THE INVENTION

Ophthalmic formulations often comprise compounds that provide desirable properties to the formulation. When these formulations are instilled in the eye, the properties of such compounds can help prevent ophthalmic problems such as bioadhesion and the formation of friction-induced tissue damage, as well as encourage the natural healing and restoration of previously damaged tissues.

Formulations are typically developed with a target viscosity to ensure that they are comfortable for the user and do not cause undesirable side effects such as blurring. A suitable formulation viscosity can help ensure that an ophthalmic formulation used in dry eye disorders will relieve dry eye-associated symptoms and/or treat the underlying disorder. In drug delivery applications the viscosity of ophthalmic formulations may be chosen to ensure that a pharmaceutical agent carried in the formulation remains in the eye for a desired length of time. Given its criticality, the viscosity of ophthalmic formulations should remain as stable as possible over time.

The viscosity of formulations can be affected by storage conditions (e.g., environmental temperature, time of storage, ambient light, etc.). Also, ophthalmic formulations must be sterilized before use, and the sterilization process, particularly heat sterilization, can dramatically affect the viscosity of such formulations.

Ophthalmic formulations have been previously described that utilize galactomannan-borate systems. U.S. Pat. No. 6,403,609 to Asgharian, entitled "Ophthalmic compositions containing galactomannan polymers and borate," describes such systems and is herein incorporated by reference in its entirety. The cross-linking of galactomannan and borate is responsible for the gel-forming behavior of the described formulations. Magnesium has been utilized in guar formulations to assist in the hydration of guar. See Vega-Cantu et al., "Effect of Magnesium and Iron on the Hydration and Hydrolysis of Guar Gum" *Biomacromolecules*, Vol. 7:441-445, 2006.

BRIEF SUMMARY OF THE INVENTION

Embodiments of the invention generally relate to ophthalmic formulations comprising galactomannan. The present inventors have unexpectedly discovered that diol alcohols can be included in such ophthalmic formulations to stabilize the viscosity of such solutions. The stabilization of the ophthalmic formulations by diol alcohols minimizes viscosity loss at elevated temperatures and ensures that the formulations can be stored safely for longer periods of time without viscosity loss.

Galactomannans of the present invention include, but are not limited to, galactomannans such as guar and guar derivatives. In other embodiments, the formulations of the present invention also comprise a borate source such as boric acid. Additionally, formulations of the present invention optionally comprise a pharmaceutically acceptable salt of a divalent cation such as magnesium, zinc and calcium that have also been discovered to stabilize galactomannan formulations. Preferred formulations comprise guar or a guar derivative, magnesium chloride, and sorbitol.

Formulations of the present invention may be used, among other applications, as drug delivery vehicles for ophthalmic therapeutics, artificial tear solutions, and as dry eye therapeutics.

Another embodiment of the present invention is a method for stabilizing ophthalmic formulations comprising galactomannan and borate. The method comprises adding a diol alcohol and, optionally, a pharmaceutically acceptable divalent cation salt such as magnesium chloride.

The foregoing brief summary broadly describes the features and technical advantages of certain embodiments of the present invention. Additional features and technical advantages will be described in the detailed description of the invention that follows.

DETAILED DESCRIPTION OF THE INVENTION

The formulations of the present invention comprise a galactomannan and a borate in aqueous solution. The cross-linking behavior of the galactomannan and the borate contributes to the viscosity of the formulations. The present invention is directed to the use of diol alcohols such as sorbitol and propylene glycol to stabilize the viscosity of ophthalmic formulations, presumably by modifying the cross-linking of the borate and galactomannan. The use of such diol alcohols also stabilizes the molecular weight of galactomannan polymers during sterilization of formulations comprising such polymers.

The diol alcohol sorbitol is used in preferred formulations of the present invention. However, the diol alcohol compounds that may be used with embodiments of the present invention include, but are not limited to, hydrophilic carbohydrates such as sorbitol or mannitol that comprise cis-diol groups (hydroxyl groups attached to adjacent carbon atoms). Other diol alcohol compounds of the present invention include polyethylene glycols, polypropylene glycols, and glycerol. Particularly preferred diol compounds are sorbitol and mannitol. The diol compounds are present at concentrations of about 0.5 to 5.0 w/v % in the formulations of the present invention, and are preferably present at a concentration of about 0.5 to 2.0 w/v %.

The formulations of the present invention optionally comprise a pharmaceutically acceptable divalent cation salt such as magnesium chloride. Divalent cations include, but are not limited to, magnesium, chloride, and zinc cations. Generally, concentrations of divalent cations should be greater than 0.05 w/v %, with a preferred concentration of 0.05 w/v % to 0.25 w/v %.

The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-β-D-mannopyranosyl units with α-D-galactopyranosyl units attached by (1-6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1-C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired. A galactomannan is typically present in a formulation of the present invention at a concentration of about 0.01 to about 10 w/v %, preferably at about 0.05 w/v % to about 2.0 w/v %, and most preferably at about 0.05 to about 0.5 w/v %. Preferred galactomannans of the present invention are guar, hydroxypropyl guar, and hydroxypropyl guar galactomannan. Native guar such as the guar produced by a process set forth in U.S. Patent Application Publication No. 2010/0196415 entitled "Process for Purifying Guar" filed Feb. 5, 2010 (the entire contents of which are herein incorporated by reference) is also a preferred galactomannan.

Borate is typically present at a concentration of about 0.05 to about 2.0 w/v %, and preferably about 0.1 to 1.5 w/v %. As used herein, the term "borate" refers to all pharmaceutically suitable forms of borates, including but not limited to boric acid, and alkali metal borates such as sodium borate and potassium borate. Boric acid is the preferred borate used with embodiments of the present invention.

Borate compounds which may be used in the compositions of the present invention are boric acid and other pharmaceutically acceptable salts such as sodium borate (borax) and potassium borate. As used herein, the term "borate" refers to all pharmaceutically suitable forms of borates. Borates are common excipients in ophthalmic formulations due to weak buffering capacity at physiological pH and well known safety and compatibility with a wide range of drugs and preservatives. Borates also have inherent bacteriostatic and fungistatic properties, and therefore aid in the preservation of the compositions.

The formulations of the present invention may optionally comprise one or more additional excipients and/or one or more additional active ingredients. Excipients commonly used in pharmaceutical formulations include, but are not limited to, demulcents, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, and preferably cross-linked polyacrylic acid and mixtures of those products.

Demulcents used with embodiments of the present invention include, but are not limited to, glycerin, polyvinyl pyrrolidone, polyethylene oxide, polyethylene glycol, propylene glycol and polyacrylic acid. Particularly preferred demulcents are propylene glycol and polyethylene glycol 400.

Suitable tonicity-adjusting agents include, but are not limited to, mannitol, sodium chloride, glycerin, and the like. Suitable buffering agents include, but are not limited to, phosphates, acetates and the like, and amino alcohols such as 2-amino-2-methyl-1-propanol (AMP). Suitable surfactants include, but are not limited to, ionic and nonionic surfactants (though nonionic surfactants are preferred), RLM 100, POE 20 cetylstearyl ethers such as Procol® CS20, poloxamers such as Pluronic® F68, and block copolymers such as poly(oxyethylene)-poly(oxybutylene) compounds set forth in U.S. Patent Application Publication No. 2008/0138310 entitled "Use of PEO-PBO Block Copolymers in Ophthalmic Compositions" filed Dec. 10, 2007 (the entire contents of which are herein incorporated by reference).

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, or sorbic acid. In certain embodiments, the formulation may be self-preserved so that no preservation agent is required.

Formulations of the present invention are ophthalmically suitable for application to a subject's eyes. The term "aqueous" typically denotes an aqueous formulation wherein the excipient is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

The formulations of the present invention are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

The compositions of the present invention can also be used to administer pharmaceutically active compounds. Such compounds include, but are not limited to, glaucoma therapeutics, pain relievers, anti-inflammatory and anti-allergy medications, and anti-microbials. More specific examples of pharmaceutically active compounds include betaxolol, timolol, pilocarpine, carbonic anhydrase inhibitors and prostglandins; dopaminergic antagonists; post-surgical antihypertensive agents, such as para-amino clonidine (apraclonidine); anti-infectives such as ciprofloxacin, moxifloxacin, and tobramycin; non-steroidal and steroidal anti-inflammatories, such as naproxen, diclofenac, nepafenac, suprofen, ketorolac, tetrahydrocortisol and dexamethasone; dry eye therapeutics such as PDE4 inhibitors; and anti-allergy medications such as H1/H4 inhibitors, H4 inhibitors, and olopatadine.

It is also contemplated that the concentrations of the ingredients comprising the formulations of the present invention can vary. A person of ordinary skill in the art would understand that the concentrations can vary depending on the addition, substitution, and/or subtraction of ingredients in a given formulation.

Preferred formulations are prepared using a buffering system that maintains the formulation at a pH of about 6.5 to a pH of about 8.0. Topical formulations (particularly topical ophthalmic formulations, as noted above) are preferred which have a physiological pH matching the tissue to which the formulation will be applied or dispensed.

In particular embodiments, a formulation of the present invention is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or greater frequency. Such dosing frequency is also maintained for a varying duration of time depending on the therapeutic regimen. The duration of a particular therapeutic regimen may vary from one-time dosing to a regimen that extends for months or years. One of ordinary skill in the art would be familiar with determining a therapeutic regimen for a specific indication.

The following examples are presented to further illustrate selected embodiments of the present invention.

EXAMPLES

Example 1 is a formulation according to an embodiment of the present invention. Example 2 summarizes studies performed on formulations of the present invention.

Example 1

| Ingredient | % w/v |
| --- | --- |
| Hydroxypropyl Guar Galactomannan | 0.25 |
| Boric Acid | 1.0 |
| Sorbitol | 1.0 |
| Polyethylene Glycol | 0.4 |
| Propylene Glycol | 0.3 |
| Potassium Chloride | 0.12 |
| Sodium Chloride | 0.35 |
| Polyquaternium-1 | 0.001 + 10% excess |
| 2-Amino-2-methylpropanol | 0.57 |
| Sodium Hydroxide/Hydrochloric Acid | q.s. pH 7.9 |
| Purified Water | q.s. 100% |

Example 2

Formulation Studies

The viscosity of various solutions of the present invention and control solutions was evaluated using a controlled stress rheometer (AR 2000ex, TA Instruments, Inc.). The measurement system was a 40 mm acrylic 2° cone and plate with a sample volume of 0.58 mL. A temperature of 25° C. +/−0.1° C. was maintained and a cover was placed over the measurement system to prevent evaporation of the solutions.

Three variables were investigated in these experiments and the results summarized in Table 1 below. Solution 89A is the control for this experiment. The dissolved $O_2$ level at ambient conditions is constant at 7 ppm. The initial viscosity of Solution 89A at a shear rate of $10\ s^{-1}$ is at 10.97 cP. After 5 weeks at room temperature, there is a small drop in viscosity of 3.65%. After 5 weeks at elevated temperatures of 40° C. there is a much greater drop in viscosity of 14.77%.

Solution 89B has the highest initial viscosity of the formulations tested. 89B is the formulation with just the removal of dissolved $O_2$. The initial viscosity of solution 89B at a shear rate of $10\ s^{-1}$ is 17.62 cP. After 5 weeks at room temperature, there is a small drop in viscosity of 3.22%. After 5 weeks at 40° C., there is a much greater drop in viscosity of 15.95%. 89B has a similar breakdown through the stability. However the initial viscosity is maintained at a level of 0.1 ppm dissolved $O_2$.

Solution 89C has 0.19 w/v % $MgCl_2$ added to the formulation. The initial viscosity of solution 89C at a shear rate of $10\ s^{-1}$ is 14.55 cP. After 5 weeks at room temperature, there is a small drop in viscosity of 1.51%. After 5 weeks at 40° C., there is a drop in viscosity of 7.97%. Solution 89C with magnesium demonstrates a greater initial viscosity and enhanced stability compared to the control solution (solution 89A) at both room and elevated temperature.

Solution 89D comprising 1.0 w/v % sorbitol shows the best stability of the tested formulations. The initial viscosity of solution 89D at a shear rate of $10\ s^{-1}$ is 13.30 cP. After 5 weeks at room temperature there is a small drop in viscosity of 0.68%. After 5 weeks at 40° C. there is a drop in viscosity of 2.85%.

TABLE 1

Summary of Viscosity Studies

| | Formulation Chemical (% wt/% wt) | | | |
| --- | --- | --- | --- | --- |
| | 13478-89A | 13478-89B | 13478-89D | 13478-89E |
| Hydroxypropyl Guar Galactomannan | 0.25 | 0.25 | 0.25 | 0.25 |
| Polyquaternium-1 | 0.001 | 0.001 | 0.001 | 0.001 |
| Boric Acid | 1.0 | 1.0 | 1.0 | 1.0 |
| Sodium Chloride | 0.35 | 0.35 | 0.35 | 0.35 |
| Sorbitol | — | — | — | 1.0 |
| $O_2$ level (ppm) | 7 | 0.1 | 7 | 7 |
| $MgCl_2 \times 6H_2O$ | — | — | 0.19 | — |
| pH | 7.0 | 7.0 | 7.0 | 7.0 |
| Purified Water | QS | QS | QS | QS |
| Initial Viscosity at $10\ s^{-1}$ (cP) | 10.97 | 17.62 | 14.55 | 13.30 |
| 5 week % Viscosity Reduction at RT | 3.65 | 3.223 | 1.51 | 0.68 |
| 5 week % Viscosity Reduction at 40° C. | 14.77 | 15.95 | 7.97 | 2.85 |

Various diol alcohols were added to a guar and borate formulation (Test Formulation shown in Table 2 below) to assess the stability of the formulation (as indicated by viscosity). Samples were heated to 78° C. for 15 hours and the viscosities were measured using the technique described above. The results are summarized in Table 3 and indicate that diol alcohols are effective stabilizers of guar and borate solutions, reducing the loss of viscosity by approximately 50% compared to the control formulation.

TABLE 2

Test Formulation

| Component | Concentration |
| --- | --- |
| Hydroxypropyl Guar Galactomannan | 0.15% |
| Boric Acid | 1% |
| Sodium Chloride | 0.35% |
| Polyquad | 0.001% |
| HCl | Adjust to pH 7.0 |
| NaOH | Adjust to pH 7.0 |
| Water | q.s. |

TABLE 3

Diol Alcohol Viscosity Study Results

| Diol Alcohol Added (3.9 mM) | % viscosity loss |
| --- | --- |
| none | 24.1 |
| Propylene Glycol | 13.2 |
| Sorbitol | 12.2 |
| Mannitol | 12.4 |
| m-Inositol | 11.6 |
| Trehalose | 11.6 |

Example 3

Molecular Weight Studies

Native guar with a molecular weight of 3.0M Daltons manufactured according to the process described in U.S. Patent Application Publication No. 2010/0196415 (previously incorporated by reference) was formulated in test formulations A-C set forth in Table 4 below. Following sterilization by autoclaving, the molecular weight of native guar in each formulation was measured. Compared to formulations B and C, the native guar in formulation A not containing a diol compound (sorbitol or glycerol) had a significantly lower measured molecular weight. The use of diol compounds in the guar formulations has a preservation effect on the molecular weight of guar during the sterilization process.

TABLE 4

Summary of Molecular Weight Study

| | Formulation Chemical (% w/v) | | |
| --- | --- | --- | --- |
| | A | B | C |
| Native Guar | 0.5 | 0.5 | 0.5 |
| Sorbitol | — | 1 | — |
| Glycerol | — | — | 1 |
| Purified Water | QS | QS | QS |
| pH | 8 | 8 | 8 |
| Native Guar Molecular Weight after Autoclaving (M Daltons) | 1.9 | 2.5 | 2.5 |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A viscosity-stabilized ophthalmic formulation comprising a galactomannan, borate and sorbitol, and wherein said galactomannan is guar or hydroxypropylguar, and wherein the said galactomannan is present in a concentration of about 0.1 w/v % to about 2.0 w/v % and said borate is present at a concentration of about 0.2 w/v % to about 2.0 w/v % and said sorbitol is present at a concentration of about 0.5% w/v % to about 5.0 w/v %.

2. A formulation according to claim 1 wherein said galactomannan is present at a concentration of about 0.05 w/v % to about 0.5 w/v % and said borate is present at a concentration of about 0.1 w/v % to about 1.5 w/v %.

3. A formulation according to claim 1 wherein said sorbitol is present at a concentration of about 0.5 w/v % to about 2.0 w/v %.

4. A formulation according to claim 1 further comprising a pharmaceutically acceptable salt of magnesium, calcium, zinc, or combinations thereof.

5. A formulation according to claim 4 wherein said salt is magnesium chloride at a concentration of about 0.05 w/v % to about 0.25 w/v %.

6. In an ophthalmic formulation comprising a galactomannan and borate, the improvement comprising adding sorbitol to stabilize the viscosity of the formulation, and wherein the said galactomannan is present in a concentration of about 0.1 w/v % to about 2.0 w/v % and said borate is present at a concentration of about 0.2 w/v % to about 2.0 w/v % and said sorbitol is present at a concentration of about 0.5% w/v % to about 5.0 w/v %.

7. A formulation according to claim 6, said formulation further comprising a pharmaceutically acceptable salt of magnesium, calcium, zinc, or combinations thereof.

8. A formulation according to claim 7 wherein the salt is magnesium chloride at a concentration of about 0.05 w/v % to about 0.25 w/v %.

9. A method for lubricating the eye comprising administering to the eye a formulation of claim 1.

10. A method for delivering a pharmaceutically active agent to the eye comprising:
    administering to the eye a formulation of claim 1 further comprising a pharmaceutically active agent.

11. A method for manufacturing a sterile ophthalmic formulation comprising:
    preparing an ophthalmic formulation comprising galactomannan and borate, wherein the said galactomannan is present in a concentration of about 0.1 w/v % to about 2.0 w/v % and said borate is present at a concentration of about 0.2 w/v % to about 2.0 w/v %;
    adding sorbitol at a concentration of about 0.5% w/v % to about 5.0 w/v % to stabilize the viscosity of the formulation to form a stabilized ophthalmic formulation; and
    sterilizing the stabilized ophthalmic formulation.

12. A method according to claim 11 wherein said galactomannan is present at a concentration of about 0.05 w/v % to about 0.5 w/v % and said borate is present at a concentration of about 0.7 w/v %.

13. A method according to claim 11 wherein said galactomannan is selected from the group consisting of:
    guar, hydroxylpropyl guar, and combinations thereof.

14. A method according to claim 11, said formulation further comprising a pharmaceutically acceptable salt of magnesium, calcium, zinc, or combinations thereof.

15. A method according to claim 14 wherein said salt is magnesium chloride at a concentration of about 0.05 w/v % to about 0.25 w/v %.

* * * * *